United States Patent

Martinez et al.

[11] Patent Number: 4,687,759
[45] Date of Patent: Aug. 18, 1987

[54] TRIPEPTIDE AND TETRAPEPTIDE ESTERS WHICH INHIBIT GASTRIC SECRETION, PROCESS FOR THEIR PREPARATION AND PHARMACEUTICAL COMPOSITIONS IN WHICH THEY ARE PRESENT

[75] Inventors: Jean Martinez, Caux; Jean-Piérre Bali, Saint-Gely-du-Fesc; Richard Magous, Lunel; Bertrand Castro, Saint-Aunes; Henri Demarne, Montpellier, all of France

[73] Assignees: Sanofi; Centre National de la Recherche Scientifique (CNRS), both of Paris, France

[21] Appl. No.: 808,959

[22] Filed: Dec. 16, 1985

[30] Foreign Application Priority Data

Dec. 20, 1984 [FR] France .................. 84 19545

[51] Int. Cl.$^4$ .................. A61K 37/43; C07K 5/08
[52] U.S. Cl. .................. 514/18; 530/331
[58] Field of Search .................. 530/330, 331; 514/18

[56] References Cited

U.S. PATENT DOCUMENTS

| | | | |
|---|---|---|---|
| 3,875,137 | 4/1975 | Jones et al. | 530/331 |
| 3,896,103 | 7/1975 | Hardy et al. | 530/330 |
| 4,012,367 | 3/1977 | Mazur | 530/330 |
| 4,172,130 | 10/1979 | Kisfaludy et al. | 530/330 |
| 4,530,837 | 7/1985 | Charon et al. | 530/330 |

FOREIGN PATENT DOCUMENTS 2226181 11/1974 France.

OTHER PUBLICATIONS

Journal of Chemistry, vol. 28, No. 3, Mar. 11, 1985.
Chemical Abstracts, vol. 94, No. 9, Mar. 1981.

*Primary Examiner*—Delbert R. Phillips
*Attorney, Agent, or Firm*—Bacon & Thomas

[57] ABSTRACT

The invention relates to the peptides of the formula:

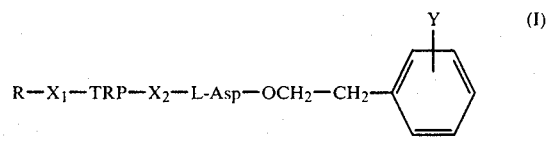

in which:
R represents hydrogen or a protecting group for the terminal amine group, such as t-butoxycarbonyl (Boc), benzyloxycarbonyl (Z) or lower alkanoyl;
$X_1$ represents either beta-Ala or a direct bond between R and the terminal amine group of the amino acid TRP;
TRP denotes either the L isomer or the D isomer of tryptophan;
$X_2$ represents L-leucine, L-methionine or L-norleucine; and
Y denotes hydrogen, a halogen atom (preferably fluorine or chlorine), a trifluoromethyl group, a cyano group or a nitro group.

These peptides inhibit gastric secretion.

6 Claims, No Drawings

TRIPEPTIDE AND TETRAPEPTIDE ESTERS WHICH INHIBIT GASTRIC SECRETION, PROCESS FOR THEIR PREPARATION AND PHARMACEUTICAL COMPOSITIONS IN WHICH THEY ARE PRESENT

The present invention relates to new peptides which inhibit gastric secretion. It also relates to a process for their preparation and pharmaceutical compositions in which they are present.

Gastrin is a gastrointestinal hormone which is capable to a high degree of stimulating gastric secretion. Furthermore, pentagastrin and tetragastrin are synthetic peptides similar to the terminal C sequence of the last 5 or 4 amino acids of gastrin and correspond respectively to the formulae:

and

the alpha-amino acids and the protecting groups being designated using the 3-letter abbreviations recommended by the IUPAC-IUB Commission on Nomenclature.

These compounds also stimulate gastric secretion.

According to the present invention, it has been found, surprisingly, that peptide derivatives of these sequences become powerful inhibitors of gastric secretion by removal of the terminal phenylalaninamide and appropriate esterification of the carboxyl group in the alpha-position of the aspartic acid.

The compounds according to the invention correspond to the general formula:

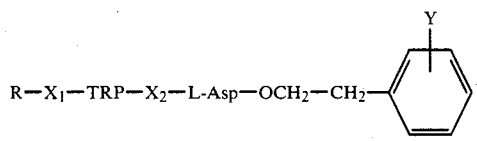

in which:

R represents hydrogen or a protecting group for the terminal amine group, such as t-butoxycarbonyl (Boc), benzyloxycarbonyl (Z) or lower alkanoyl;

$X_1$ represents either beta-Ala or a direct bond between R and the terminal amine group of the amino acid TRP;

TRP denotes either the L isomer or the D isomer of tryptophan;

$X_2$ represents L-leucine, L-methionine or L-norleucine; and

Y denotes hydrogen, a halogen atom (preferably fluorine or chlorine), a trifluoromethyl group, a cyano group or a nitro group.

The compounds according to the invention can be prepared by the usual techniques for peptide synthesis, either in the solid phase by Merrifield's method or in the liquid phase.

Starting from the alpha-ester of aspartic acid, the different amino acids present in the sequence are introduced in succession. The coupling reactions are carried out either with an activated ester of the amino acid to be introduced, in dimethylformamide and in the presence of diisopropylethylamine and 1-hydroxybenzotriazole, or with the amino acid itself, in which case the reaction is carried out in dimethylformamide and in the presence of diisopropylethylamine and benzotriazolyloxytris-dimethylaminophosphonium hexafluorophosphate (BOP).

All the amino acids are incorporated in the form of the derivative protected on the amine in the alpha-position, the chosen protecting group being the t-butoxycarbonyl group. If the amino acid used has reactive groups in its side chain, these must be blocked beforehand. Thus, the acid groups in the beta-position of the aspartic acid must be blocked in the form of an ester, in particular the benzyl ester.

After each coupling reaction, deprotection of the amine in the alpha-position is effected by acid hydrolysis.

Finally, the peptides, protected on their groups in the side chains, are partially or completely deprotected to give the compounds of the formula (I).

The starting alpha-ester of aspartic acid is prepared from aspartic acid protected on the amine by a tert.-butoxycarbonyl group and on the acid group in the beta-position by a benzyl ester.

The esterification in the alpha-position can be carried out either by reaction with an optionally substituted phenethyl halide or by reaction with the corresponding phenethyl alcohol in the presence of dicyclohexylcarbodiimide and paradimethylaminopyridine.

The non-limiting examples which follow will provide a better understanding of the invention. The following abbreviations will be used in these examples:

Amino acids and protecting groups

Asp: L-aspartic acid
beta-Ala: beta-alanine
Leu: L-Leucine
L-Trp: L-tryptophan
D-Trp: D-tryptophan
Boc: tert.-butoxycarbonyl
OBzl: benzylester

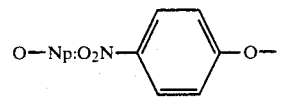

Other abbreviations:

DMF: dimethylformamide
DCC: dicyclohexylcarbodiimide
DIEA: diisopropylethylamine
TFA: trifluoroacetic acid
HOBt: 1-hydroxybenzotriazole

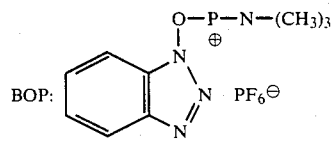

EXAMPLE 1

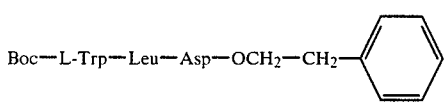
(a)

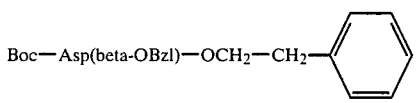

4.55 g of the cesium salt of the acid Boc-Asp-(beta-OBzl)-OH are dissolved in 100 ml of DMF, 2.22 g of phenethyl bromide are then added and the mixture is stirred for 12 hours at room temperature. It is concentrated in vacuo at a temperature below 40° C. and the residue is then dissolved in 250 ml of ethyl acetate. The solution is washed with a saturated solution of sodium bicarbonate, water, a 10% solution of citric acid and then water again. The solution is dried over sodium sulfate and the solvent is evaporated off in vacuo.

The residue crystallizes from an ether/hexane mixture. Yield 85%; melting point=58-60° C.; $[\alpha]_D = -20.7°$ (c=1.06, DMF).

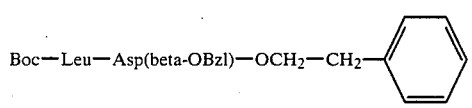
(b)

4.27 g of the product obtained above are dissolved in 20 ml of TFA and the solution is left for ½ hour at room temperature. It is evaporated in vacuo with ether being added and the temperature being kept below 40° C. The operation is repeated several times. The oily residue is triturated with ether and then dried in vacuo over potassium hydroxide.

2.32 g of the trifluoroacetate thus obtained are dissolved in 10 ml of DMF with 1.21 g of Boc-leu, 2.2 g of BOP and 1.8 ml of DIEA.

The mixture is left for 8 hours at room temperature and then concentrated in vacuo at a temperature below 40° C. The residue is dissolved in 200 ml of ethyl acetate and the resulting solution is washed successively with a saturated solution of sodium bicarbonate, water, a 10% solution of citric acid and water again. The solution is dried over sodium sulfate and then concentrated in vacuo. The residue is chromatographed on silica gel. Elution with an ethyl acetate/hexane mixture 1/1 vol/vol gives a colorless oil (2.48 g). Yield 92%; $[\alpha]_D = 19.9°$ (c=0.93, DMF).

Thin layer chromatography

Rf=0.95 (ethyl acetate/hexane 8/2 vol/vol)

Rf=0.91 (acetone/hexane 7/3 vol/vol).

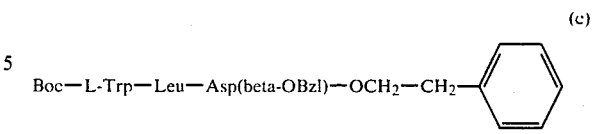
(c)

2 g of the product obtained under (b) are treated with 10 ml of TFA for 30 minutes. The mixture is evaporated several times in the presence of ether. The oily residue is triturated with ether and then dried in vacuo over potassium hydroxide. The trifluoroacetate is dissolved in 20 ml of DMF with 1.7 g of Boc-L-Trp-ONp, 0.63 g of HOBt and 1.6 ml of DIEA.

The mixture is left overnight at room temperature and then treated as indicated in paragraph (b).

Chromatography on silica gel, using a hexane/ethyl acetate mixture 3/7 vol/vol as the eluent, gives the expected product (2.36 g), which crystallizes from ether. Melting point=135°-138° C; $[\alpha]_D = -24°$ (c=1.3, DMF); yield 88%.

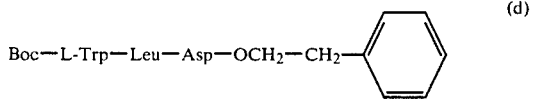
(d)

0.73 g of the product obtained under (c) is dissolved in 50 ml of 95° ethanol and the solution is hydrogenated, at ordinary temperature and pressure, in the presence of 0.07 g of 10% palladium-on-charcoal.

The reaction has ended after 4 hours. The catalyst is filtered off and the filtrate is concentrated in vacuo at a temperature below 40° C.

The residue is triturated with an ether/hexane mixture to give a colorless powder (0.483 g). Melting point=95°-100° C.; $[\alpha]_D = 22.7°$ (c=1.3, DMF); yield 76%.

EXAMPLE 2

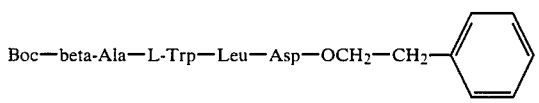

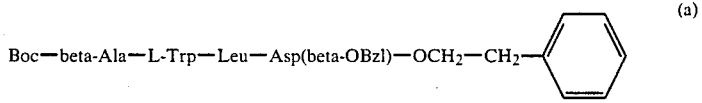
(a)

0.73 g of the product obtained in Example 1(c) is treated with 3 ml of TFA as indicated above. After drying, the trifluoroacetate thus obtained is dissolved in 10 ml of DMF with 0.189 g of Boc-beta-Ala, 0.398 g of BOP and 0.4 ml of DIEA.

The mixture is left overnight at room temperature and treated as in Example 1(b). Chromatography on silica gel, using an ethyl acetate/hexane mixture 7/3 vol/vol as the eluent, gives the expected product (0.595 g), which crystallizes on trituration with ether. Melting point=163°-166° C; $[\alpha]_D = -18.9°$ (c=1.2, DMF); yield 83%.

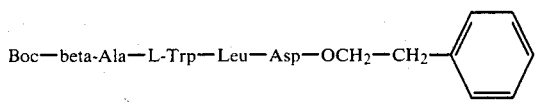

0.398 g of the product obtained above is hydrogenated according to the procedure of Example 1(d). A colorless powder is isolated in the same way. Melting point=100°-103° C; $[\alpha]_D = -17.7°$ (c=1.7, DM); yield 79%.

EXAMPLE 3

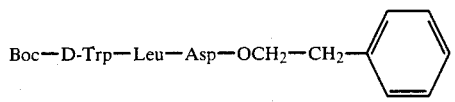

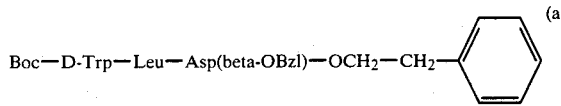

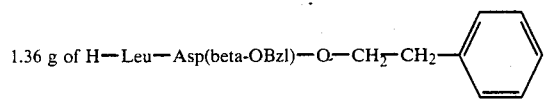

trifluoroacetate (prepared according to Example 1) are dissolved in 20 ml of DMF with 1.06 g of BOP, 0.76 g of Boc-D-Trp and 0.86 ml of DIEA.

After 8 hours at room temperature, the mixture is treated as indicated in Example 1(b). The mixture is chromatographed on silica gel and elution with an ethyl acetate/hexane mixture 5/5 vol/vol isolates the expected product, which crystallizes on trituration with an ether/hexane mixture. Melting point=67°-70° C.; $[\alpha]_D = -14.1°$ (c=1, DMF); yield 91%.

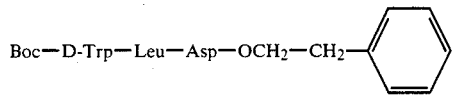

0.242 g of the product obtained above is hydrogenated as indicated in Example 1(d). A colorless powder is isolated in the same way. Melting point=108°-110° C.; $[\alpha]_D = -15.8°$ (c=1, DMF); yield 78%.

EXAMPLE 4

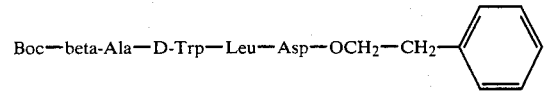

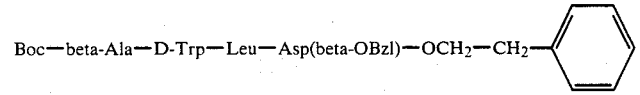

The procedure of Example 2(a) is followed starting from the protected peptide of Example 3(a). The same treatment, followed by chromatography on silica gel using an ethyl acetate/hexane mixture 1/1 vol/vol as the eluent, gives a colorless powder. Melting point=1-53 -156° C.; $[\alpha]_D = -27.8°$ (c=1.4, DMF); yield 79%.

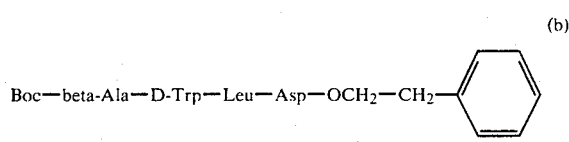

The previous product is hydrogenated by the process described in Example 1(d) to give a colorless powder. Melting point=105°-110° C.; $[\alpha]_D = -20.4°$ (c=1.2, DMF); yield 84%.

EXAMPLE 5

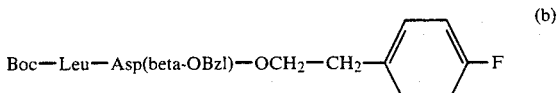

2.2 g of Boc-Asp(beta-OBzl)—OH are dissolved in 70 ml of methylene chloride with 0.924 g of parafluorophenethyl alcohol, 1.24 g of DCC and 0.732 g of 4-dimethylaminopyridine. The mixture is left overnight at room temperature, the dicyclohexylurea is then filtered off and the filtrate is concentrated in vacuo.

The residue is taken up in ethyl acetate. The solution is washed successively with a saturated solution of sodium bicarbonate, water, a 10% solution of citric acid and water again. The solution is dried over sodium sulfate and the solvent is evaporated off in vacuo. The residue is chromatographed on a column of silica gel. Elution with a hexane/ethyl acetate mixture 8/2 vol/vol gives a colorless oil (1.82 g). $[\alpha]_D = -16°$ (c=1.9, DMF); yield 68%.

Thin layer chromatography

Rf=0.64 (chloroform)
Rf=0.85 (ethyl acetate/hexane 1/1 vol/vol).

The procedure of Example 1(b) is followed,

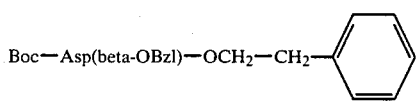

being replaced with an equivalent quantity of

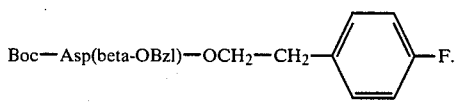

The same treatment, followed by chromatography on silica gel using a hexane/ethyl acetate mixture 8/2 vol/vol as the eluent, gives a colorless oil with a yield of 89%. $[\alpha]_D = -18.5°$ (c=0.9, DMF).

Thin layer chromatography

Rf=0.66 (chloroform)
Rf=0.59 (ethyl acetate/hexane 1/1 vol/vol).

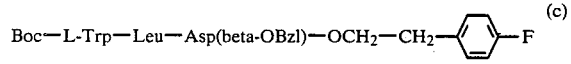

(c)

The procedure of Example 1(c) is followed starting from the product obtained above. The same treatment, followed by chromatography on silica gel, gives a crystalline product. Melting point=90°-92° C.; $[\alpha]_D = -23°$ (c=1.2, DMF); yield 77%.

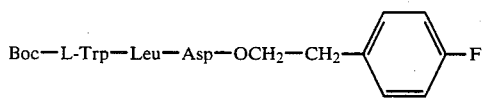

(d)

The product obtained above is hydrogenated in the presence of palladium-on-charcoal, as indicated previously. The same treatment gives a solid. Melting point=103°-107° C.; $[\alpha]_D = -19°$ (c=1, DMF); yield 72%.

EXAMPLE 6

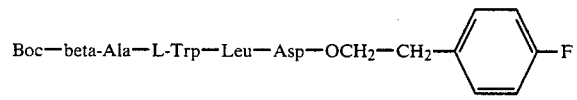

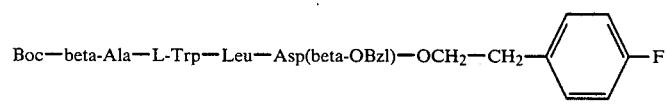

(a)

The procedure of Example 2(a) is followed starting from the protected peptide of Example 5(c). The expected product is obtained in the same way. Melting point=80°-85° C. (decomposition).

Thin layer chromatography

Rf=0.5 (ethyl acetate/hexane 7/3 vol/vol).

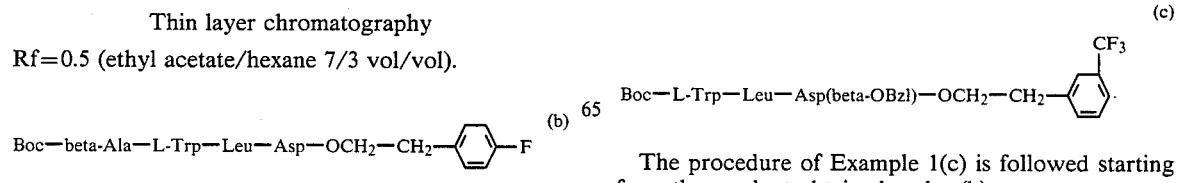

(b)

The peptide obtained above is deprotected by catalytic hydrogenation as indicated in Example 1(d).

A solid is obtained. Melting point=110°-115° C. (decomposition).

Thin layer chromatography

Rf=0.82 (ethyl acetate/pyridine/acetic acid/water 80/20/3/3 vol/vol).

EXAMPLE 7

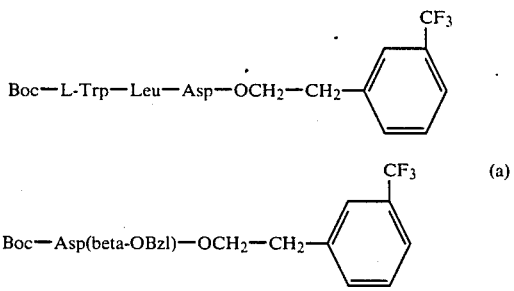

(a)

The procedure of Example 5(a) is followed, the parafluorophenethyl alcohol being replaced with an equivalent quantity of metatrifluoromethylphenethyl alcohol.

Chromatography on silica gel, using a hexane/ethyl acetate mixture 2/8 vol/vol as the eluent, gives an oil. $[\alpha]_D = -12.9°$ (c=0.8, DMF); yield 71%.

Thin layer chromatography

Rf=0.67 (chloroform)
Rf=0.69 (ethyl acetate/hexane 1/1 vol/vol).

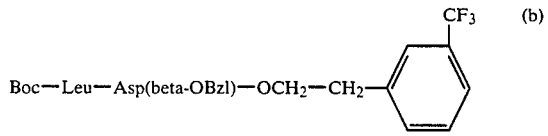

(b)

The procedure of Example 1(b) is followed starting from the ester prepared above. Chromatography on a column of silica gel, using an ethyl acetate/hexane mixture 1/1 vol/vol as the eluent, gives a crystalline product. Melting point=72°-75° C.; $[\alpha]_D = -18°$ (c=1.1, DMF); yield 78%.

(c)

The procedure of Example 1(c) is followed starting from the product obtained under (b).

Chromatography on a column of silica gel, using an ethyl acetate/hexane mixture 1/1 vol/vol as the eluent, gives a colorless powder. Melting point=55°-60° C.; $[\alpha]_D = -5.6°$ (c=1.9, DMF); yield 81%.

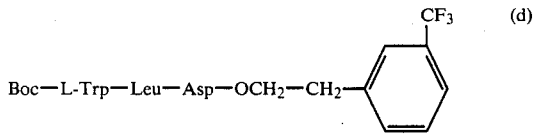
(d)

The product obtained in paragraph (c) is deprotected by catalytic hydrogenation as indicated in Example 1(d).

A solid is obtained from an ether/hexane mixture. Melting point=95°-100° C.; $[\alpha]_D = -19.6°$ (c=0.9, DMF); yield 79%.

The compounds according to the invention were studied for their therapeutic properties. More particularly, these compounds were studied in vivo for their effect on gastric secretion in rats.

The model chosen for measuring the effect on secretion is reperfused anesthetized rat's stomach. The photocol adopted is a modified version of the one previously described by Ghosh and Schild.

A 300 g male rat of the Wistar strain, fasted for 18 hours, is anesthetized with urethane (10% solution, 1.5 ml/100 g, i.p.). A tracheotomy is then performed and a catheter is passed through the vein in the penis to allow the i.v. administration of the peptides. A cannula is then placed in the esophagus as far as the cardia and a second is placed in the duodenum (by means of a duodenotomy performed about 3 cm from the pylorus) as far as the gastric antral region.

A propionic/succinic acid solution (pH 5.5), which gives a linear variation in the pH as a function of the concentration of H+ ions, is used to perfuse the stomach in open or closed circuit at a rate of 3 ml/minute. The body temperature and the solution temperature are monitored and kept at 30° C. The secretion of acid from the stomach causes a pH change, which is detected by a glass electrode and recorded as a function of time. After stabilization of the basal secretion, gastrin is injected intravenously, either by perfusion or by a single injection. The response is recorded as a function of time and the quantity of acid secreted is measured on the recording chart as the difference relative to the basal secretion.

The same experiment is carried out either by i.v. injection of the peptide to be studied on a plateau of acid secretion stimulated by gastrin, or by association of the peptide with the stimulant in variable concentration ratios.

By varying the dose of the product to be studied and measuring the corresponding effects, it is possible to determine for each product the 50% effective dose, or the dose which causes a 50% inhibition of the gastric secretion induced by gastrin.

The results obtained with different products of the invention are as follows:

| Peptide | ED$_{50}$ (mg/kg) |
| --- | --- |
| Example 1 | 0.1 |
| Example 2 | 0.04 |
| Example 4 | 0.2 |
| Example 5 | 0.08 |
| Example 6 | 0.02 |

-continued

| Peptide | ED$_{50}$ (mg/kg) |
| --- | --- |
| Example 7 | 0.5 |

These results show that the compounds according to the invention have a very substantial inhibitory effect on gastric secretion. Furthermore, these compounds have a low toxicity.

Consequently, the compounds according to the invention may be used in human therapy in all cases where gastric secretion can usefully be reduced, and in particular for the treatment of gastroduodenal ulcers.

The compounds of the present invention are preferably administered by intravenous, intramuscular or subcutaneous injection. They are used in a solvent such as physiological serum (isotonic saline solution).

The dosage can vary according to the desired intensity of the therapeutic effect, the severity of the complaint to be treated and the method of administration used. It must therefore be determined for each patient according to these various criteria. It is most commonly between 0.1 and 10 mg of active principle per kg of body weight.

The invention therefore also relates to the pharmaceutical compositions in which a peptide according to the invention is present as the active ingredient, in combination with a pharmaceutically acceptable vehicle such as physiological serum.

What is claimed is:

1. A peptide of the formula:

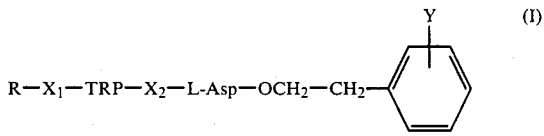
(I)

in which:
R represents hydrogen or a protecting group for the terminal amine group;
X$_1$ represents either beta-Ala or a direct bond between R and the terminal amine group of the amino acid TRP;
TRP denotes either the L isomer or the D isomer of tryptophan;
X$_2$ represents L-leucine, L-methionine or L-norleucine; and
Y denotes hydrogen, a halogen atom, a trifluoromethyl group, a cyano group or a nitro group.

2. A peptide as claimed in claim 1, which is one of the following peptides:

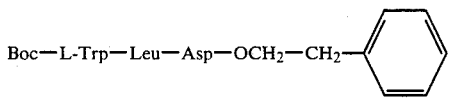

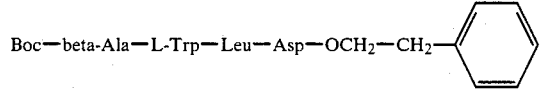

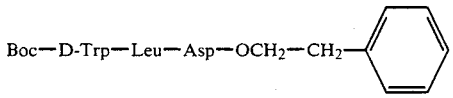

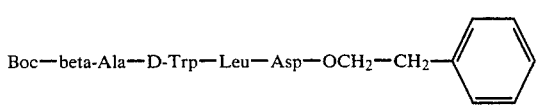

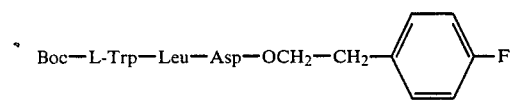

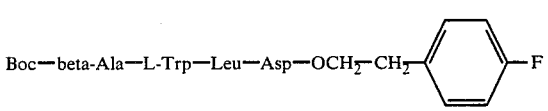

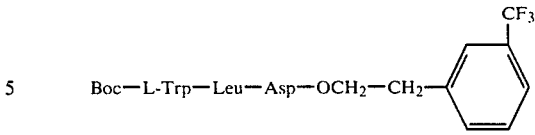

or the corresponding deprotected peptide.

3. A peptide as claimed in claim 1 wherein R is a protecting group which is t-butoxycarbonyl, benzyloxycarbonyl or lower alkanoyl.

4. A peptide as claimed in claim 1 wherein Y is a halogen atom which is a fluorine or chlorine atom.

5. A peptide as claimed in claim 3 wherein Y is a halogen atom which is a fluorine or chlorine atom.

6. A pharmaceutical composition for inhibiting gastric secretion which contains, as active ingredient, an effective amount for inhibiting gastric secretion of a peptide as claimed in claim 1 in association with a pharmaceutically acceptable vehicle.

* * * * *